United States Patent [19]

Benson et al.

[11] 4,013,762
[45] Mar. 22, 1977

[54] GROWTH PROMOTION

[75] Inventors: Harvey D. Benson, Cincinnati; Joyce Francis Grunwell, Hamilton; John O'Neal Johnston, Cincinnati, all of Ohio; Vladimir Petrow, Chapel Hill, N.C.

[73] Assignee: Richardson-Merrell Inc., Wilton, Conn.

[22] Filed: May 10, 1976

[21] Appl. No.: 684,947

[52] U.S. Cl. .................................. 424/242; 424/243
[51] Int. Cl.² .......................................... A61K 31/56
[58] Field of Search ........................... 424/242, 243; 260/397.4

[56] References Cited

UNITED STATES PATENTS

| | | | |
|---|---|---|---|
| 2,945,765 | 7/1960 | Snyder et al. | 99/4 |
| 3,449,381 | 6/1969 | Bowers | 260/397.4 |
| 3,666,858 | 5/1972 | Hughes et al. | 424/243 |
| 3,737,535 | 6/1973 | Brethour | 424/243 |

*Primary Examiner*—Elbert L. Roberts
*Attorney, Agent, or Firm*—L. Ruth Hattan; Eugene O. Retter; George W. Rauchfuss, Jr.

[57] ABSTRACT

A method of promoting the growth of ruminants and poultry without concommitant adrogenizing effects using the following compound:

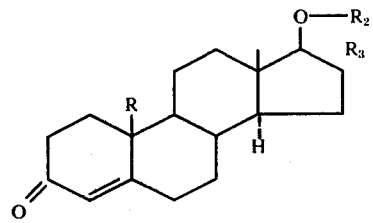

wherein R is —CHO or —$CH_2OR_1$; each of $R_1$ and $R_2$ is hydrogen, alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or cycloalkylcarbonyl wherein the cycloalkyl moiety has from 5 to 10 carbon atoms; $R_3$ is hydrogen; or $R_2$ and $R_3$ together form a double bond between the 17- position carbon atom and the oxygen atom.

11 Claims, No Drawings

GROWTH PROMOTION

FIELD OF INVENTION

This invention relates to methods of promoting the growth of ruminants and poultry without concommitant androgenizing effects.

BACKGROUND OF INVENTION

A number of agents are known to be useful in promoting growth and weight gain in domestic animals. Certain agents, for example, compositions containing α-hydroxy-γ-methylmercaptobutyric acid described in U.S. Pat. No. 2,745,745 issued May 15, 1956, are known to promote growth by improving feed efficiency. Other agents such as, for example, anti-bacterial agents are said to be useful in promoting growth of animals which may be the result of removing a restriction on normal growth. Estrogens, or estrogenic substances, progestogens and androgens, particularly testosterone propionate are also known to be useful in promoting growth in animals. It is reported that the weight gain in steroid fed, for example, estrogen fed poultry is likely the result of increased fat depositions. In ruminants it is reported that increased weight gains resulting from the administration of steroids is likely due to the anabolic effect of the steroids since there is an increase in muscle tissue and bone in such animals with less fat in the carcasses. Although testosterone propionate is known to be effective in promoting growth in animals the use of said compound results in masculinization of the muscle fiber due to the androgenicity of the compound. The compounds employed in the present invention provide a method of promoting the growth of poultry and ruminants without any masculinizing effect on the muscle fiber.

Some of the compounds employed in the present invention, for example, 19-hydroxyandrost-4-ene-3,17-dione and the 19-oxo derivative thereof have been involved in numerous in vitro studies wherein their role in the metabolism of androgen has been investigated. Additionally, 19-hydroxyandrost-4-ene-3,17-dione is reported to have been administered to two healthy male subjects each twenty-one years of age (J. Clin. Endocrinol. Metab. 28, 1401 (1968)). In U.S. Pat. No. 3,235,573, issued Feb. 15, 1966, and U.S. Pat. No. 3,449,381, issued June 10, 1969, is reported 3-oxo-17β-hydroxyandrost-4-en-19-al wherein the utilities disclosed are anabolic-androgenic activity, inhibition of pituitary gonadotrophins and adrenocorticotrophin, antiestrogenic, blood, liver and adrenal cholesterol lowering properties, control of fertility and psychotic conditions, and appetite stimulants. Although 3-oxo-17β-hydroxyandrost-4-en-19-al has been reported to have anabolic-androgenic activity the present invention would not be suggested thereby in view of our findings that said compound is effective in growth promotion in animals without any masculinizing effect on the muscle fiber which would be an indication of a lack of or only limited androgenic effects.

SUMMARY OF INVENTION

This invention relates to a method of promoting growth in poultry and ruminants by administering a compound of the following general formula:

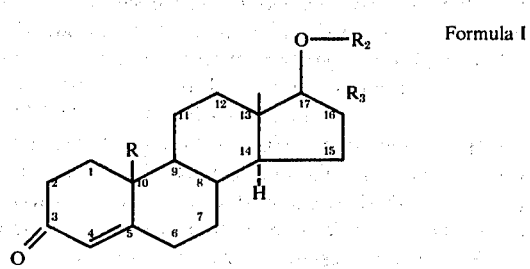

Formula I wherein R is —CHO or —CH$_2$OR$_1$; each of R$_1$ and R$_2$ is hydrogen, alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or cycloalkylcarbonyl wherein the cycloalkyl moiety has from 5 to 10 carbon atoms; R$_3$ is hydrogen; or R$_2$ and R$_3$ together form a double bond between the 17-position carbon atom and the oxygen atom.

DETAILED DESCRIPTION OF INVENTION

In the compounds of general Formula I the term alkylcarbonyl is taken to mean a group of the structure alkyl

wherein the alkyl moiety has from 1 to 20 carbon atoms and can be a straight chain or a branched chain. Illustrative examples of the alkyl moiety in the substituent alkylcarbonyl group are methyl, ethyl, n-propyl, isopropyl, n-butyl, sec-butyl, tert-butyl, n-pentyl, neopentyl, pivalyl, hexyl, heptyl, octyl, 2,4-dimethyloctyl, undecyl, 9-methylundecyl, pentadecyl, decyl, octadecyl, nonadecyl and didecyl.

The term benzoyl as used in reference to the compounds of general Formula I is taken to mean the group

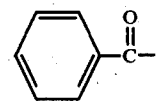

The term phenylalkylcarbonyl as used in reference to the compounds of general Formula I is taken to mean a substituent group of the structure

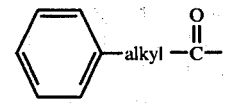

wherein the alkyl moiety, which may also be referred to as an alkylene moiety, has from 1 to 6 carbon atoms and can be a straight chain or a branched chain. Illustrative examples of the alkyl moiety in the substituent phenylalkylcarbonyl group are methyl, ethyl, n-propyl, n-butyl, n-pentyl, hexyl, isopropyl, sec-butyl, tert-butyl and neopentyl.

Illustrative examples of cycloalkylcarbonyl groups which R$_1$ and R$_2$ may be are cyclopentanecarbonyl, cyclohexanecarbonyl, cyclooctanecarbonyl, 1- or 2-norbornanecarbonyl and 1- or 2-adamantanecarbonyl.

It is apparent from the foregoing general Formula I that the compounds employed in the instant invention are androst-4-ene-3,17-diones having a —$CH_2OR_1$ or —CHO group at the 10$\beta$-position as represented respectively by the following general Formulas II and III, or are 17$\beta$-hydroxyandrost-4-en-3-one derivatives or esters thereof as defined by $R_2$ having a —$CH_2OR_1$ or —CHO group present at the 10$\beta$-position as represented respectively by the following general Formulas IV and V:

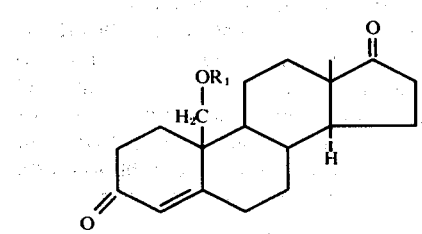

Formula II

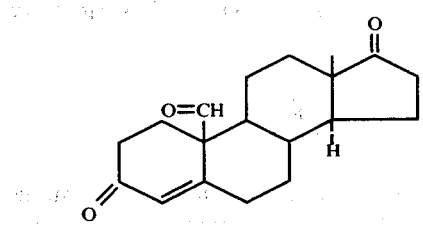

Formula III

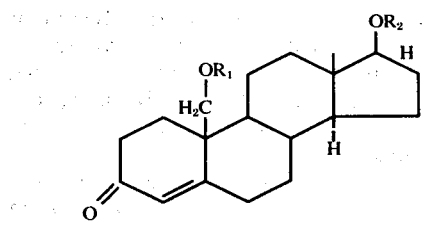

Formula IV

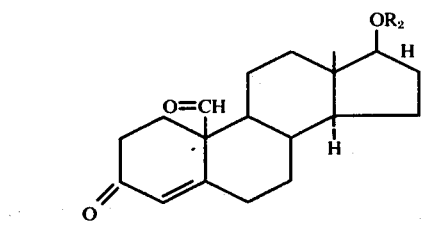

Formula V

In general Formulas II and IV $R_1$ is hydrogen or alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or cycloalkylcarbonyl wherein the cycloalkyl moiety has from 5 to 10 carbon atoms as defined hereinabove.

In general Formulas IV and V the hydrogen atom attached to the 17- position is in the alpha position, and $R_2$ is hydrogen or alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or, cycloalkylcarbonyl wherein the cycloalkyl moiety has from 5 to 10 carbon atoms as defined hereinabove.

The use of the compounds as represented by each of general Formulas II and III in promoting the growth of poultry and ruminants represents a preferred embodiment of this invention with the use of the compounds of general Formula III being a more specifically preferred embodiment. Other embodiments of this invention are the use of the compounds as represented by general Formulas IV and V in promoting the growth of poultry and ruminants with the use of the compounds of general Formula IV wherein $R_1$ and $R_2$ each represent hydrogen and the compounds of general Formula V wherein $R_2$ represents hydrogen being more preferred embodiments.

Illustrative examples of compounds employed in the present invention are 17$\beta$,19-bis-(1-oxopropoxy)androst-4-en-3-one, 17$\beta$,19-bis-(1-oxodidecyloxy)androst-4-en-3-one, 17$\beta$,19-dihydroxyandrost-4-en-3-one, 19-hydroxy-17$\beta$-(1-oxopropoxy)androst-4-en-3-one, 19-hydroxy-17$\beta$-(1-oxohexadecyloxy)androst-4-en-3-one, 19-acetoxyandrost-4-ene-3,17-dione, 19-acetoxy-17$\beta$-hydroxyandrost-4-en-3-one, 3-oxo17$\beta$-hydroxyandrost-4-en-19-al, 19-(1-adamantanylcarbonyloxy)androst-4-ene-3,17-dione, 19-(1-norbornylcarbonyloxy)androst-4-ene-3,17-dione, 19-(1-cyclopentylcarbonyloxy)-androst-4-ene-3,17-dione, 3,17-dioxoandrost-4-en-19-al and 3-oxo-17$\beta$-(1-adamantanylcarbonyloxy)androst-4-en-19-al.

The compounds of general Formula I are effective in promoting the growth and weight gain in poultry and ruminants. Although the exact mechanism of action is not known it is believed that the weight gain or increased growth in poultry is due to increased fat depositions, and in ruminants is due to increased muscle fiber. Although in ruminants administration of the compounds result in increased muscle fiber which may be a reflection of an anabolic effect of the compounds the present method of promoting growth does not result in a masculinization of the muscle fiber as is reported to occur with other androgens, for example, testosterone propionate. Masculinization of the muscle fiber as reported to occur with testosterone and esters thereof lowers the quality of the meat of the animals thus, the present invention offers an improved method of promoting growth in that the compounds employed herein are essentially devoid of masculinizing effects.

As used herein the term poultry is taken to mean chickens and turkeys, and the term ruminants is taken to mean bovine animals or cattle and sheep.

The compounds of general Formula I can be incorporated into animal feeds or can be admixed with other dietary supplements as a feed concentrate to be incorporated into a feed ration. Descriptions of suitable feeds and feed concentrates can be found in the book "Feeds and Feeding" by F. B. Morrison, published by the Morrison Publishing Co. of Ithaca, New York, 1948, ed. 21. The selection of the particular feed is within the knowledge of the art and will depend on the animal, the economics, natural materials available, and the nature of the effect desired. The compounds employed herein may also be administered in the drinking water of the animal, or can be administered by way of an implant or injection suitably formulated.

The feed compositions of this invention are comprised of conventional animal feedstuff fortified with from about 0.05 to 1.0% by weight of the compound of general Formula I. Within this range for best growth promotion it is preferred that poultry feed compositions contain from 0.05 to 0.2% by weight of the compound on a finished feed basis. In preparing feed rations for ruminants it is preferred that the finished feed contain from 0.5 to 1.0% by weight of the compound of general formula I. The particular concentration of the compound in the finished feed will depend on the age and condition of the animal being fed. A particular important composition according to this feature of the invention is a concentrate suitable for preparation and sale for addition to animal feedstuffs in an appropriate amount. These concentrates ordinarily will comprise about 1% to about 95% of the compound of general Formula I together with a diluent. Generally the diluent will consist of a solid such as ground corn, ground wheat, ground barley, ground oats, wheat bran, soybean oil meal, cottonseed meal, linseed meal or cottonseed hulls. The feed compositions and concentrates may also contain proteins, carbohydrates, fats, vitamins, minerals or antibiotics.

The following illustrate suitable feed compositions and concentrates or supplements.

| Poultry Feed Ingredient | Lbs./ton |
|---|---|
| Ground yellow corn | 1215 |
| Stabilized fat | 110 |
| De-hulled soybean meal | 400 |
| Fish meal | 150 |
| Corn gluten meal | 72 |
| Defluorinated phosphate | 20 |
| Ground limestone | 6 |
| Salt | 9 |
| Vitamin and mineral premix | 6 |
| 3,17-Dioxoandrost-4-en-19-al | 12 |

| Ingredient | Parts by Weight |
|---|---|
| Salt, iodized | 36 |
| Vitamin A and D mix | 20 |
| Trace mineral mix | 4 |
| Soy mill feed | 125 |
| 3,17-Dioxoandrost-4-en-19-al | 15 |

| Ruminant Supplement Ingredient | Parts by Weight |
|---|---|
| Soybean meal | 1200 |
| Cane molasses | 260 |
| Dehydrated alfalfa meal | 260 |
| Dicalcium phosphate | 104 |
| Salt, iodized | 36 |
| 3,17-Dioxoandrost-4-en-19-al | 140 |

| Ruminant Supplement Ingredient | Parts by Weight |
|---|---|
| Cane molasses | 250 |
| Dehydrated alfalfa meal | 880 |
| Urea | 430 |
| Dicalcium phosphate | 200 |
| Salt, iodized | 70 |
| 3,17-Dioxoandrost-4-en-19-al | 140 |

A solution or suspension of the compounds of general Formula I can be prepared for administration using a liquid carrier such as water or oils, such as petroleum or soybean oil. Also, the compounds of general Formula I can be administered as a crystalline implant. For injection or implant the amount of compound employed will vary from 0.001 to 10 mg/kg. In ruminants a suitable amount of compound for implant or injection can be from 25 to 1,000 mg. Illustratively 100 mg of a compound of general Formula I as a compressed crystalline implant can be placed, for example, at the base of an ear of the animal. In poultry a suitable amount of compound of general Formula I for implant or injection can be from 1 mg to 50 mg. Illustratively, 10 mg of a compound of general Formula I as a compressed crystalline implant can be placed in the neck of the animal.

Although as indicated hereinabove it is believed that the compounds employed herein are effective as growth promoters primarily due to increasing fat depositions in poultry and increasing muscle fiber in ruminants, it has also been found that the compounds employed herein result in pancreatic beta-cell hypertrophy with an accompanying increase in insulin production when administered to mammals. Therefore, the compounds employed herein may be used to enhance insulin production in mannals and additionally increase appetite, food intake and fattening.

The data contained in the following Table I demonstrate the effectiveness of the compounds of general Formual I as growth promoters. The data contained in Table I were obtained by treating ten day old leghorn chicks of an average weight of 100 g subcutaneously for six days with 1.0, 10, and 30 mg/kg/day of 3,17-dioxoandrost-4-en-19-al. The weight gain during one week as compared to untreated control chicks indicates that the compound induced a significant increase in growth rate as measured by weight gain.

TABLE I

Chick Weight Gain

| Treatment | Dose (mg/kg) | Weight Gain (g ± S.E.M.) |
|---|---|---|
| Control | — | 52.7 ± 1.6 |
| 3,17-Dioxoandrost-4-en-19-al | 1 | 58.8 ± 1.4* |
| 3,17-Dioxoandrost-4-en-19-al | 10 | 63.0 ± 1.1* |
| 3,17-Dioxoandrost-4-en-19-al | 30 | 74.0 ± 2.6* |

*Significantly different from controls, $p < 0.05$

The data contained in the following Table II indicate that the compounds of general Formula I do not bind in vitro with the androgen receptor of androgen target tissue. This binding is the first step necessary for hormonal action. To obtain these data male rats were castrated and the prostate cytosol was prepared 24 to 48 hours postsurgery. Concentrations of $4 \times 10^{-6}$ to $4 \times 10^{-10}$ molar were compared for competitive bindings of $H^3$-testosterone labeled cytosol receptor sites according to the methods of Leavitt et al., Endocrin. 94, 1041 (1974) and Korenman, J. Clin. Endocrin. and Metab. 28, 127 (1968). The relative binding of 3,17-dioxoandrost-4-en-19-al was compared with testosterone and 5α-dihydrotestosterone which was equated to 100.

TABLE II

Androgen Binding

| Compound | % Binding |
|---|---|
| 5α-Dihydrotestosterone | 100.0 |
| Testosterone | 40.0 |
| 3,17-Dioxoandrost-4-en-19-al | 0.07 |

The lack of androgen binding affinity of 3,17-dioxoandrost-4-en-19-al supports the finding of lack of certan androgenic side effects, for example, masculinizing effects of the muscle fiber, of the compounds employed in the present invention.

Many of the compounds employed in the present invention are known in the art or are commercially available. For example, 19-hydroxyandrost-4-ene-3,17-dione, 17β,19-dihydroxyandrost-4-en-3-one, 19- hydroxy17β-(1-oxoethoxy)androst-4-en-3-one, 19-hydroxy-17β-(1-oxobenzyloxy)androst-4-en-3-one and 3-oxo-17β-(1-oxobenzyloxy)androst-4-en-19-al are commercially available.

The esters of the compounds employed in the present invention, that is, compounds wherein either or both of $R_1$ and $R_2$ are alkylcarbonyl wherein the alkyl moiety has from 1 to 20 carbon atoms and is straight or branched, cycloalkylcarbonyl wherein the cycloalkyl moiety has from 5 to 10 carbon atoms, benzoyl and phenylaklycarbonyl wherein the alkyl moiety has from 1 to 6 carbon atoms and is straight or branched can be prepared as follows although other methods may also be employed. Ester derivatives of 19-hydroxyandrost-4-ene-3,17-dione and bis-ester derivatives of 17β-19-dihydroxyandrost4-en-3-one are prepared by reacting the corresponding 19-hydroxy or 17β,19-dihydroxy compound with an appropriate acid anhydride of the formula

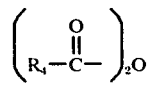

or acid chloride of the formula

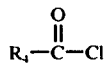

wherein $R_4$ is an alkyl group of from 1 to 20 carbon atoms and is straight or branched, a cycloalkyl group of from 5 to 10 carbon atoms, phenyl or phenylalkyl wherein the alkyl moiety has from 1 to 6 carbon atoms and is straight or branched in the presence of a base such as pyridine, quinoline or trialkylamine, such as, triethylamine, which base serves as the solvent, for from 1 to 24 hours at a temperature of from about 25° C to 100° C. The appropriate acid anhydride or acid chloride are known in the art or can be prepared from the corresponding acids by procedures well known in the art.

Compounds employed in the present invention wherein $R_1$ is hydrogen and $R_2$ forms an ester group are prepared from the above obtained 17β,19-diester derivatives by refluxing the diester with one equivalent of sodium bicarbonate or potassium bicarbonate or one-half equivalent of sodium carbonate or potassium carbonate or dilute sodium hydroxide or potassium hydroxide solution in a lower alcohol solvent such as methanol or ethanol and water for about one hour, the reflux temperature depending on the solvent system employed.

Compounds employed in the present invention wherein R is CHO and $R_2$ forms an ester group are prepared by dissolving the above obtained compounds wherein $R_1$ is hydrogen and $R_2$ forms an ester group in acetone cooled to 0° to 10° C and treating the solution with sufficient Jones reagent to effect the oxidation. Jones reagent is prepared by standard procedures using 26.72 grams of chromium trioxide, 23 ml of concentrated sulfuric acid and water to make 100 ml. The Jones reagent can be added to the solution until the reddish brown color persists which requires about 289 ml. Other oxidizing agents can be used, such as, dicyclohexylcarbodiimide in dimethylsulfoxide.

The following specific examples further illustrate the preparation of compounds employed in the instant invention.

EXAMPLE 1

17β,19-Bis(1-oxopropoxy)androst-4-en-3-one

A solution of 10 g of 17β,19-dihydroxyandrost-4-en-3-one which is commerically available and 25 ml of propionic anhydride in 200 ml of pyridine is allowed to stand overnight after which 100 ml of ethanol is added, and the reaction mixture is stirred for one hour. The mixture is then poured into one liter of water and the solid product is collected by filtration. The solid is dissolved in ether, dried over magnesium sulfate, filtered and the solvent removed. The residue is dissolved in hot hexane and allowed to cool yielding 17β,19-bis(1-oxopropoxy)androst-4-en-3-one. M.P. 82°–84° C.

EXAMPLE 2

17β,19-Dihydroxyandrost-4-en-3-one

A solution of 150 g of 19-hydroxyandrost-4-en-3-one in 6 liters of ethanol is cooled in an ice bath. To this cold solution is added 13.5 g of potassium borohydride, and the reaction mixture is stirred for two hours at about 0° C after which a second 13.5 g or potassium borohydride is added. Two hours later a third 13.5 g portion of potassium borohydride is added to the reaction mixture which is stirred for an additional one hour then poured into 11 liters of water to which 70 ml of acetic acid is added. The ethanol is distilled off under reduced pressure and the aqueous residue cooled to 0° C. The solid which separates is filtered off, dried and dissolved in 25 liters of hot chloroform after which the temperature is adjusted to 25° C. To the chloroform solution is added 250 g of manganese dioxide, and the mixture is stirred for two hours then filtered and the solvents removed under reduced pressure. The solid residue is recrystallized from acetonitrile to give 17β,19-dihydroxyandrost-4-en-3-one. M.P. 205°–207° C.

EXAMPLE 3

19-Hydroxy-17β(1-oxopropoxy)androst-4-en-3-one

A solution of 11 g of 17β,19-bis(1-oxopropoxy)androst-4-en-3-one in 2 liters of methanol is treated with 2.5 g of sodium carbonate in 250 ml of water and refluxed for one hour after which the reaction mixture is poured into 10 liters of water, and the solid collected by filtration. The solid is dissolved in methylene chloride, dried over magnesium sulfate, filtered and the solvent removed. The residue is crystallized from acetone-hexane yielding 6 g of 19-hydroxy-17β(1-oxopropoxy)androst-4-en-3-one. M.P. 160°–162° C.

EXAMPLE 4

19-Acetoxyandrost-4-ene-3,17-dione

A solution of 19-hydroxyandrost-4-ene-3,17-dione in acetic anhydride and pyridine is allowed to stand overnight after which the reaction mixture is poured into ice water. The resulting solid is collected, dried and recrystallized from hexane to give 19-acetoxyandrost-4-ene-3,17-dione.

EXAMPLE 5

19-Acetoxy-17β-hydroxyandrost-4-en-3-one

To a solution of 25.6 g of 19-acetoxyandrost-4-ene-3,17-dione in 4 liters of methanol cooled to 0° C is added 3.1 g of sodium borohydride, and the mixture is stirred at 0° C for 1 hour after which 30 ml of acetic acid is added and the methanol removed under reduced pressure. The resulting residue is taken up in ethyl acetate and washed with water. The organic layer is dried over magnesium sulfate, filtered and the solvent removed. The solid residue is dissolved in 2 liters of chloroform treated with 125 g of manganese dioxide and stirred for two hours. The reaction mixture is filtered, and the solvent removed under reduced pressure. The residue is chromatagraphed on alumina using benzene-ether (1:1) as the eluant. The product is recrystallized from acetone-hexane to give 19-acetoxy-17β-hydroxyandrost-4-en-3-one, M.P. 125°–127° C.

EXAMPLE 6

19-Hydroxy-17β(2'-tetrahydropyranyloxy)androst-4-en-3-one

To a solution of 10 g of 19-acetoxy-17β-hydroxyandrost4-en-3-one in 300 ml of dihydropyran is added a small crystal of p-toluene sulfonic acid. The reaction mixture is allowed to stand overnight after which it is dissolved in ether and extracted with dilute sodium bicarbonate. The ether layer is dried over magnesium sulfate, filtered and the solvent removed. The resulting residue is dissolved in 2 liters of methanol and 2.5 g of sodium bicarbonate in 250 ml of water is added. The methanol solution is refluxed for one hour after which the solvent is removed under reduced pressure at 40° C. The residue is covered with water, and the solid crude product collected and recrystallized from ethylacetate yielding 19-hydroxy-17β(2'-tetrahydropyranyloxy)androst-4-en-3-one. M.P. 193°–199° C.

EXAMPLE 7

3-Oxo-17β-hydroxyandrost-4-en-19-al

A solution of 7 g of 19-hydroxy-17β-(2'-tetrahydropyranyloxy)androst-4-en-3-one in 500 ml of acetone is cooled to 10° C and 5.3 ml of Jones reagent is added dropwise. The reaction is stirred for an additional 10 minutes then poured into water and extracted with ethylacetate. The ethylacetate extract is dried over magnesium sulfate, filtered and the solvent removed under reduced pressure. The residue is dissolved in 250 ml of 95% ethanol and 2 ml of concentrated hydrochloridic acid is added. The ethanol solution is refluxed with one hour then cooled to room temperature and neutralized with solid sodium carbonate. The neutralized solution is diluted with water and extracted with ethyl acetate. The extract is dried over magnesium sulfate, filtered and the solvent removed leaving a residue which is chromatagraphed on alumina using 25% ether in benzene as the eluant to give the product 3-oxo-17β-hydroxyandrost-4-en-19-al, M.P. 125–127° C.

EXAMPLE 8

19-(1-Adamantanylcarbonyloxy)androst-4-ene-3,17-dione

A solution of 22 g of 19-hydroxyandrost-4-ene-3,17-dione, 18 g of 1-adamantanecarboxylic acid chloride, and 29 ml of pyridine in 2.2 liters of toluene is refluxed overnight. The reaction mixture is cooled, and the toluene layer is washed with water, dried over magnesium sulfate and filtered then the solvent is removed. The resulting residue is crystallized from methanol to give 19-(1-adamantanylcarbonyloxy)androst-4-ene-3,17-dione, M.P. 161°–163° C.

EXAMPLE 9

3,17-Dioxoandrost-4-en-19-al

To a solution of 30 g of 19-hydroxyandrost-4-ene3,17-dione in 3 liters of acetone cooled in an ice bath is added 28 ml of Jones reagent over a 1 hour period. The reaction mixture is stirred for an additional fifteen minutes, filtered and the solvent removed under reduced pressure at 35° C. The residue is taken up in a large volume of ether and 1.5 liters of water. The ether layer is collected, dried over magnesium sulfate, filtered and the solvent removed The residue is crystallized from acetone-hexane to give 3,17-dioxoandrost-4-en-19-al, M.P. 126°–129° C.

EXAMPLE 10

3-Oxo-17β-(1-oxopropoxy)androst-4-en-19-al

To a solution of 14 g of 19-hydroxy-17β-(1-oxopropoxy)androst-4-en-3-one in 1 liter of acetone cooled in an ice bath is added 13.3 ml of Jones reagent over 1 hour after which the reaction mixture is poured into a large volume of water and extracted with ether. The ether extract is dried over magnesium sulfate, filtered and the solvent removed. The residue is crystallized from acetone-hexane to give 3-oxo-17β(1-oxopropoxy)androst-4-en-19-al, M.P. 119°–121° C.

We claim:

1. A method of promoting the growth of poultry and ruminants which comprises administering thereto a growth promoting effective amount of a compound of the formula:

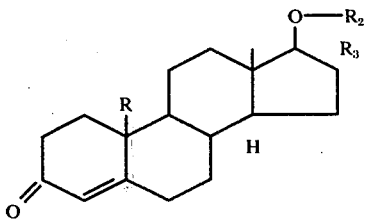

wherein R is —CHO or —CH$_2$OR$_1$; each of R$_1$ and R$_2$ is hydrogen, alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or cycloalkylcarbonyl wherein the cycloalkyl moiety has from 5 to 10 carbon atoms; R$_3$ is hydrogen; or R$_2$ and R$_3$ together form a double bond between the 17- position carbon atom and the oxygen atom.

2. The method of claim 1 wherein comprises administering the compound in a feed composition containing from 0.05% to 1% by weight of the compound.

3. The method of claim 1 which comprises administering from 0.001 to 10 mg/kg of the compound.

4. The method of claim 3 wherein the compound is administered in an injectable form.

5. The method of claim 3 wherein the compound is administered as a crystalline implant.

6. The method of claim 1 wherein R is —CHO.

7. The method of claim 6 wherein R$_2$ and R$_3$ together form a double bond between the 17- position carbon atom and the oxygen atom.

8. The method of claim 7 wherein the compound is 3,17-dioxoandrost-4-en-19-al.

9. The method of claim 1 wherein R is —CH$_2$OR$_1$.

10. The method of claim 9 wherein R$_2$ and R$_3$ together form a double bond between the 17- position carbon atom and the oxygen atom.

11. The method of claim 10 wherein the compound is 19-hydroxyandrost-4-ene-3,17-dione.

* * * * *

UNITED STATES PATENT AND TRADEMARK OFFICE
CERTIFICATE OF CORRECTION

PATENT NO. : 4,013,762
DATED : March 22, 1977
INVENTOR(S) : H.D. Benson, J.F. Grunwell, J.O. Johnston and V. Petrow It is certified that error appears in the above-identified patent and that said Letters Patent are hereby corrected as shown below:

Abstract, line 4 " 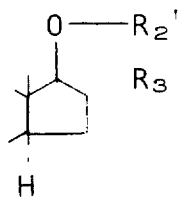 should read " 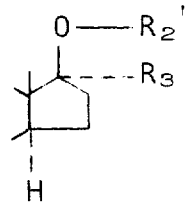.

Column 2, line 5 - Formula 1 " 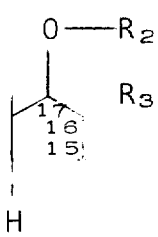 " should read

"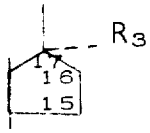"; line 26 - 30, line 26 "alkyl" line 30 "$\overset{O}{\underset{\|}{}}$" should read "alkyl-$\overset{O}{\underset{\|}{C}}$-". Column 3, line 35 - Formula IV " 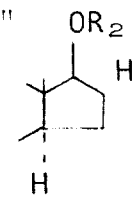 " should read " 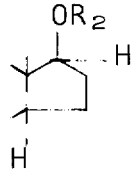 "; Column 3, line 45 - Formula V " 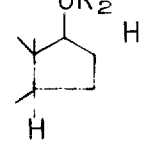 " should

UNITED STATES PATENT AND TRADEMARK OFFICE
CERTIFICATE OF CORRECTION

PATENT NO. : 4013,762
DATED : March 22, 1977
INVENTOR(S) : H.D. Benson, J.F. Grunwell, J.O. Johnston and V. Petrow It is certified that error appears in the above-identified patent and that said Letters Patent are hereby corrected as shown below.

read " 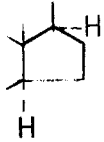 $OR_2$ ". Column 10, Claim 1, line 35 " 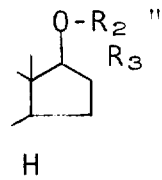 $O-R_2$ " should read " 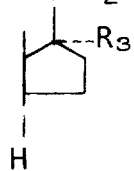 $O-R_2$ ". Column 5, line 35 should read "Ruminant Premix The following premix can be prepared to be used at a rate of about 200 lbs. / ton of finished feed." Column 6, line 12 "mannals" should read "mammals". Column 7, line 11 "phenyl-aklycarbonyl" should read "phenylalkylcarbonyl"; line 16 "androst 4-en" should read "androst-4-en". Column 10, line 49, Claim 2 "claim 1 wherein" should read "claim 1 which".

Signed and Sealed this

Thirty-first Day of January 1978

[SEAL]

Attest:

RUTH C. MASON
Attesting Officer

LUTRELLE F. PARKER
Acting Commissioner of Patents and Trademarks